United States Patent
Kroker et al.

[11] Patent Number: 5,897,749
[45] Date of Patent: Apr. 27, 1999

[54] CONTINUOUS DISTILLATIVE SEPARATION OF LIQUID MIXTURES WHICH CONTAIN (METH) ACRYLIC ACID AS THE MAIN COMPONENT

[75] Inventors: Ruprecht Kroker, Bobenheim-Roxheim; Manfred Wiedemann, Ludwigshafen, both of Germany

[73] Assignee: BASF Aktiengesellschaft, Ludwigshafen, Germany

[21] Appl. No.: 08/732,728

[22] Filed: Oct. 18, 1996

[30] Foreign Application Priority Data

Oct. 23, 1995 [DE] Germany ................................. 19539295

[51] Int. Cl.⁶ ................................. B01D 3/42; B01D 3/00; B01D 3/04; B01D 1/06
[52] U.S. Cl. ................................. 203/2; 159/27.1; 202/237; 203/25; 203/26; 203/27; 203/88; 203/DIG. 21
[58] Field of Search ................................. 202/237; 159/27.1; 203/2, 25, 26, 27, 88, DIG. 21

[56] References Cited

U.S. PATENT DOCUMENTS 4,559,108  12/1985  Ahlberg ................................. 203/26

FOREIGN PATENT DOCUMENTS 1 421 185   1/1965   France .
1 814 774  12/1969   Germany .
15 19 595   2/1970   Germany .

*Primary Examiner*—Patrick D. Niland
*Attorney, Agent, or Firm*—Oblon, Spivak, McClelland, Maier & Neustadt, P.C.

[57] ABSTRACT

Liquid mixtures which contain (meth)acrylic acid as the main component are continuously separated in a distillation apparatus which comprises a still, a condenser and a connection between still and condenser and to which the liquid mixture to be separated is continuously fed, by a process in which the energy required for evaporation of the liquid mixture is supplied to the distillation apparatus by a procedure in which a part of the liquid content of the still is continuously removed, superheated and recycled to the still.

10 Claims, 3 Drawing Sheets

CONTINUOUS DISTILLATIVE SEPARATION OF LIQUID MIXTURES WHICH CONTAIN (METH) ACRYLIC ACID AS THE MAIN COMPONENT

The present invention relates to a process for the continuous distillative separation of liquid mixtures which contain (meth)acrylic acid as the main component, in a distillation apparatus which comprises a still, a condenser and a connection between still and condenser and to which the liquid mixture to be separated is continuously fed.

(Meth)acrylic acid is used as an abbreviation and stands for acrylic acid or methacrylic acid. (Meth)acrylic acid, either as such or in the form of its esters, is important in particular for the preparation of polymers for a very wide range of uses, for example for use as adhesives, and has a high tendency to polymerize, especially in the liquid state. Safe storage of essentially pure liquid (meth)acrylic acid is possible only with the addition of polymerization inhibitor, even at lower temperatures.

(Meth)acrylic acid is obtainable, inter alia, by catalytic gas-phase oxidation of alkanes, alkanols, alkenes or alkenals which contain 3 or 4 carbon atoms. (Meth)acrylic acid is particularly advantageously obtainable, for example, by catalytic gas-phase oxidation of propene, acrolein, tert-butanol, isobutene, isobutane, isobutyraldehyde or methacrolein.

However, other possible starting compounds are those from which the actual $C_3/C_4$ starting compound is first formed as an intermediate during the gas-phase oxidation. An example is the methyl ether of tert-butanol.

These starting gases, as a rule diluted with inert gases, such as nitrogen, $CO_2$, saturated hydrocarbons and/or steam, are passed, as a mixture with oxygen, over transition metal (eg. Mo-, V-, W- and/or Fe-containing) mixed oxide catalysts at elevated temperatures (usually from 200 to 400° C.) and under atmospheric or superatmospheric pressure and are converted by oxidation into (meth)acrylic acid (cf. for example DE-A 44 05 059, EP-A 253 409, EP-A 92 097, DE-A 44 31 949).

Owing to the many parallel and secondary reactions which take place in the course of the catalytic gas-phase oxidation and because of the inert diluent gases to be concomitantly used, however, the resulting product is not pure (meth)acrylic acid but a reaction mixture which contains essentially (meth)acrylic acid, the inert diluent gases and byproducts, from which the (meth)acrylic acid must be separated off.

The (meth)acrylic acid is usually separated from the reaction mixture by extraction and distillation methods, ie. as a rule the (meth)acrylic acid formed is initially taken up from the reaction gas mixture of the gas-phase oxidation into a suitable absorbent. Separation of the absorbate by distillation then usually gives a crude (meth)acrylic acid, from which a pure (meth)acrylic acid is frequently produced by passage through further distillative separation stages (eg. DE-A 44 36 243, DE-A 44 36 243, German Patent 21 36 396, DE-A 43 08 087, EP-A 297 445, EP-A 117 146, EP-B 102 642, British Patent 1 346 737 and DE-B 2 207 184).

As a rule, the crude (meth)acrylic acid has a purity of $\geq 95$, frequently $\geq 97$, % by weight, the impurities comprising in particular lower aldehydes (eg. formaldehyde, acetaldehyde, acrolein, methacrolein, propionaldehyde, n-butyraldehyde, benzaldehyde, furfural or crotonaldehyde), water, lower alkanecarboxylic acids (eg. acetic acid and propionic acid) and anhydrides of alkanecarboxylic acids (eg. maleic anhydride). In contrast to the crude (meth)acrylic acid, the purity of the pure (meth)acrylic acid is usually $\geq 98$, frequently $\geq 99$, % by weight.

The problem of the distillative separation of liquid mixtures which contain (meth)acrylic acid as the main component (eg. $\geq 95\%$ by weight) is thus sufficiently well known.

Usually, the distillate of separation is carried out continuously in a distillation apparatus which comprises a still, a condenser and a connection between still and condenser and to which the liquid mixture to be separated is continuously fed.

An integral part of the still is usually an evaporator which transfers the energy required for evaporation indirectly via heated heat exchange surfaces to the liquid mixture to be separated by distillation.

The problem with the distillative separation of liquid mixtures which contain (meth)acrylic acid as the main component is that, regardless of whether the (meth)acrylic acid is separated off via the top or via the bottom, as a rule polymer formation occurs during the distillative separation, even in the presence of polymerization inhibitors, such as air, hydroquinone, hydroquinone monomethyl ether, paranitrosophenol, paramethoxyphenol and/or phenothiazine, owing to the high evaporation temperatures required even at reduced pressure, said polymer formation causing relatively rapid coating of, in particular, the heat exchange surface of the evaporator. This inhibits, inter alia, the heat transfer and reduces the evaporator performance, and the continuous distillation must therefore be interrupted from time to time to remove the coating (in particular with the use of tube-bundle heat exchangers which may be completely blocked as a result of the coating; the literature (for example, EP-A 648 520 and EP-A 616 998) therefore recommends nondistillative methods for the purification of crude (meth)acrylic acid).

It is an object of the present invention to provide a novel process for the continuous distillative separation of liquid mixtures which contain (meth)acrylic acid as the main component, in a distillation apparatus which comprises a still, a condenser and a connection between still and condenser and to which the liquid mixture to be separated is continuously fed, in which process the problem of coating of the evaporator surface is present to a reduced extent.

We have found that this object is achieved by a process for the continuous distillative separation of liquid mixtures which contain (meth)acrylic acid as the main component, in a distillation apparatus which comprises a still, a condenser and a connection between still and condenser and to which the liquid mixture to be separated is continuously fed, wherein at least some (as a rule at least 50%, frequently at least 75%, particularly preferably at least 100%) of the energy required for evaporation of the liquid mixture is supplied to the distillation apparatus by a procedure in which a fraction of the liquid content present at a pressure $P_x$ in the still is continuously removed, said fraction is heated to a temperature $T_y$, at a pressure $P_y$ above $P_x$, with the proviso that $T_y$, is above the boiling point $T_x$, associated with the pressure $P_x$, and below the boiling point $T_y$, associated with the pressure $P_y$, of the liquid content of the still, and that fraction of the still liquid which has been removed and superheated in this manner based on the pressure $P_x$ is then recycled to the distillation apparatus while letting down the pressure.

Figure 1:
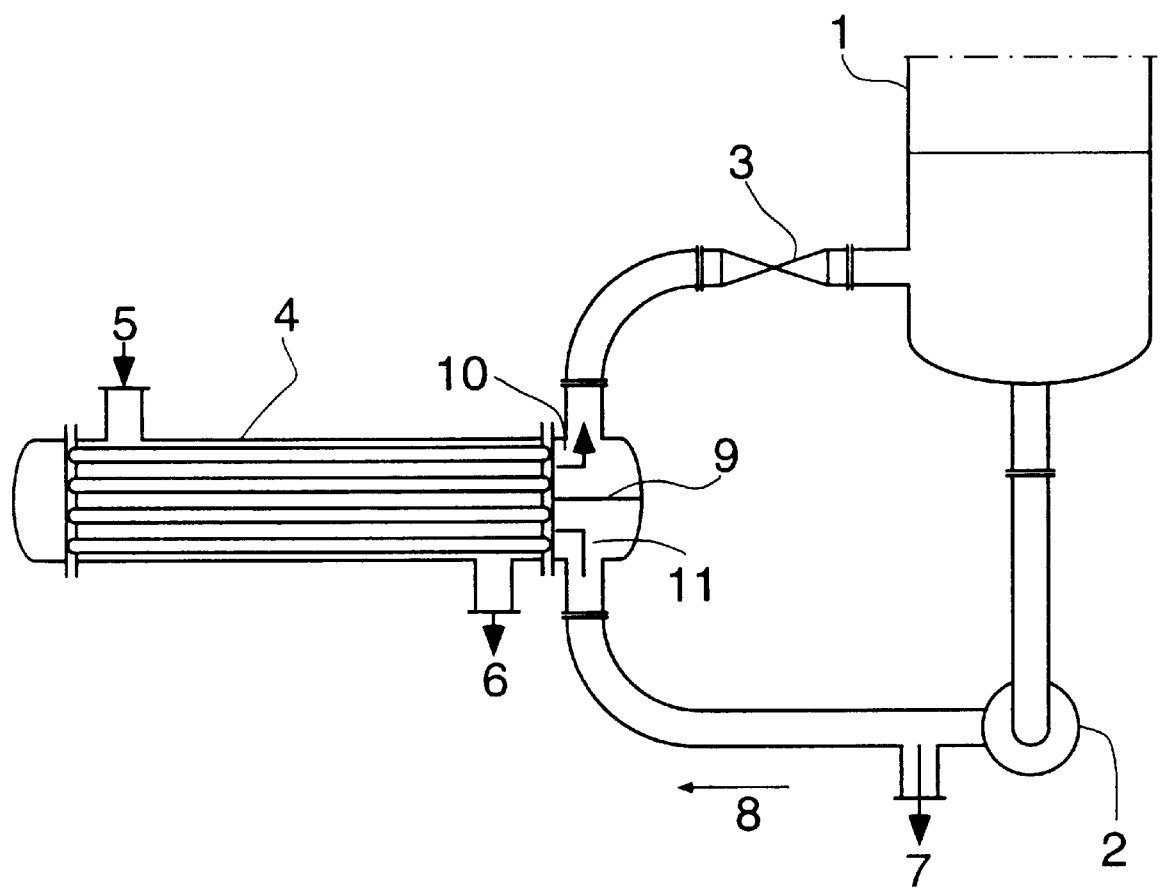
FIG. 1 shows a distillation apparatus useful for the present invention.

As further prior art, it is possible to start from the use of forced-circulation flash evaporation for reducing the incrustation on evaporator surfaces in the evaporation of mixtures in which there is increasing deposition of solids with increasing concentration (for example, Verdampfertechnik by Reinhard Billet, Hochschultaschenbücher Verlag, Bibliographisches Institut-Mannheim (1965), page 146 et seq., and Perry's Chemical Engineers Handbook, Sixth Edition, McGraw-Hill Book Company (1984), pages 11 to 32, Heat Transfer).

However, the essential difference between the novel process and the abovementioned use of the forced-circulation flash evaporation is that the tendency of (meth)acrylic acid to polymerize increases with increasing temperature, whereas the solubility of most substances increases with the temperature as a result of the entropy, ie. whereas heating a solution containing deposited solid generally reduces the amount of deposited solid in the solution, the solid deposition in liquid mixtures containing (meth)acrylic acid as the main component increases with the temperature. Furthermore, the tendency of (meth)acrylic acid in the liquid state to polymerize is likely to increase with increasing pressure. In view of this state of affairs, the advantageousness of the novel process over the prior art processes is surprising.

The novel process displays its advantageousness in the case of liquid mixtures to be separated by distillation and containing $\geq 95$, $\geq 96$, $\geq 97$, $\geq 98$ and $\geq 99\%$ by weight of (meth)acrylic acid. It may be carried out both at atmospheric pressure (1 bar) and at reduced pressure. The novel distillative separation is preferably carried out at reduced pressure (particularly preferably at from 10 to 150 mbar). The novel distillative separation can be carried out both as a single-phase flow separation (simple distillation) and as a two-phase flow separation (rectification). In principle, both a two-phase countercurrent (the ascending vapor stream is fed countercurrent to the descending reflux liquid stream in a column) and a two-phase cocurrent (the ascending vapor stream is fed cocurrent to the reflux liquid stream in a column), can be realized. In the case of a novel two-phase flow separation, the connection between still and condenser is generally formed by a rectification apparatus having baffles. Suitable such apparatuses are all column types known per se, such as tray columns, packed columns or rotary columns.

In the case of the novel single-phase flow separation, the connection between still and condenser is as a rule a column which is essentially free of baffles, with the exception of impact means (which prevent the entrainment of liquid droplets).

The liquid mixture to be separated according to the invention by distillation and containing (meth)acrylic acid as the main component can be continuously fed both directly into the still itself and into the connection between still and condenser.

The novel process is particularly suitable for the distillative purification of crude (meth)acrylic acid, as obtained by the conventional catalytic gas-phase oxidation method described at the outset. The lower aldehydic impurities which significantly increase the tendency of the (meth) acrylic acid to polymerize can thus be reduced in a manner known per se with the addition of hydrazine and/or derivatives thereof (eg. aminoguanidine bicarbonate). Furthermore, alkylbenzenesulfonic acid compounds, such as dodecylbenzenesulfonic acid, which reduce the tendency toward coating, can be added in a known manner. Suitable polymerization inhibitors are those stated at the outset, among which phenothiazine is preferred. They are used in amounts known per se (a few ppm, typically about 200 ppm, based on (meth)acrylic acid).

The novel process can be realized in a particularly simple manner by the use of a forced-circulation tubular evaporator which is mounted outside the still and separated from the still by a throttle apparatus, as shown in FIG. 1 (1=still, 2=circulation pump, 3=throttle apparatus, 4=tubular evaporator, 5=heating steam, 6=heating steam condensate, 7=bottom product outlet, 8=circulation direction, 9=separation apparatus, 10=outflow, 11=inflow).

A fraction of the liquid content present at a pressure $P_x$ in the still is continuously removed and is pumped by means of a circulation pump into the inflow pipe of a tubular evaporator (tube-bundle heat exchanger). A heating medium, for example heating steam (as a rule steam under superatmospheric pressure), whose temperature is above the temperature of the liquid content of the still, flows around the inner pipes of the tubular evaporator. On the way through the inflow and outflow pipes of the tubular evaporator, the still liquid removed is heated by indirect heat exchange to a temperature $T_y$, which is above the temperature of the liquid in the still. A throttle apparatus separates tubular evaporator and still on the pressure side and, by a suitable choice of the circulation pump delivery, makes it possible to set a throttle inlet pressure $P_y$ which is above $P_x$ and above the boiling pressure $P_{y'}$, at the temperature $T_{y'}$, of the still liquid removed.

According to the invention, it is important that boiling (bubble formation) of the circulated still liquid fraction in the pipes of the tubular evaporator is suppressed by the above measures. The circulated fraction of the still liquid is instead super-heated in the pipes of the tubular evaporator in relation to the pressure $P_x$ prevailing above the liquid content of the stills, and the boiling process is thus shifted to the emergence side of the throttle apparatus (ie. the content of the pipes of the tubular evaporator is present as a single phase, and the tubular evaporator acts merely as a superheater).

The superheated liquid may pass through the throttle apparatus into the distillation apparatus, directly into the liquid content of the still. Under these conditions, the temperature of the liquid content of the still regularly corresponds to the boiling point $T_x$ associated with the pressure $P_x$ prevailing above the still liquid.

However, in principle, the superheated liquid may also pass through the throttle apparatus into the distillation apparatus by entering the connection between still and condenser, above the liquid level of the liquid still content. Under these conditions, the temperature of the liquid content of the still is regularly below the boiling point $T_x$ associated with the pressure $P_x$ prevailing above the still liquid. What is important is that the evaporation effect of the tubular evaporator mounted outside the distillation apparatus occurs only in the distillation apparatus, ie. outside the evaporator.

Throttling can be effected, for example, mechanically (orifice plates, valves) and/or hydrostatically (by an appropriately high liquid column in the still above the emergence point of the superheated liquid).

Tubular evaporators to be used according to the invention frequently comprise from 100 to 300 V4A stainless steel pipes. The thickness of the pipe walls is often from 1 to 3 mm and the external diameter is regularly from 25 to 35 mm. Their length may be up to a few meters (typically 3 m). As a rule, hot steam under superatmospheric pressure (up to a few bar) flows around the pipes, as a heating medium. However, other conventional heating media, such as heat transfer oils and/or hot gases, may also be used. The delivery of the circulation pump is typically from 100 000 to 300 000 l/h. This results in flow velocities in the pipes of the tubular evaporator of from 1 to 7 m/sec.

In general, the heat transfer in the tubular evaporator is advantageously designed, according to the invention, so that $T_y$ is from 3 to 12K above the temperature of the liquid content of the still. The difference between $P_y$ and $P_x$ is as a rule not more than 8, often not more than 5, and frequently not more than 3, bar. It is in many cases from 0.2 to 1 bar.

The liquid mixture containing (meth)acrylic acid as the main component is fed continuously to the distillation apparatus typically in an amount of from 2000 to 4000 l/h.

A part of the high-boiling distillation residue which collects in the course of time can be removed continuously, for example via the take-off point 7.

Figure 2:
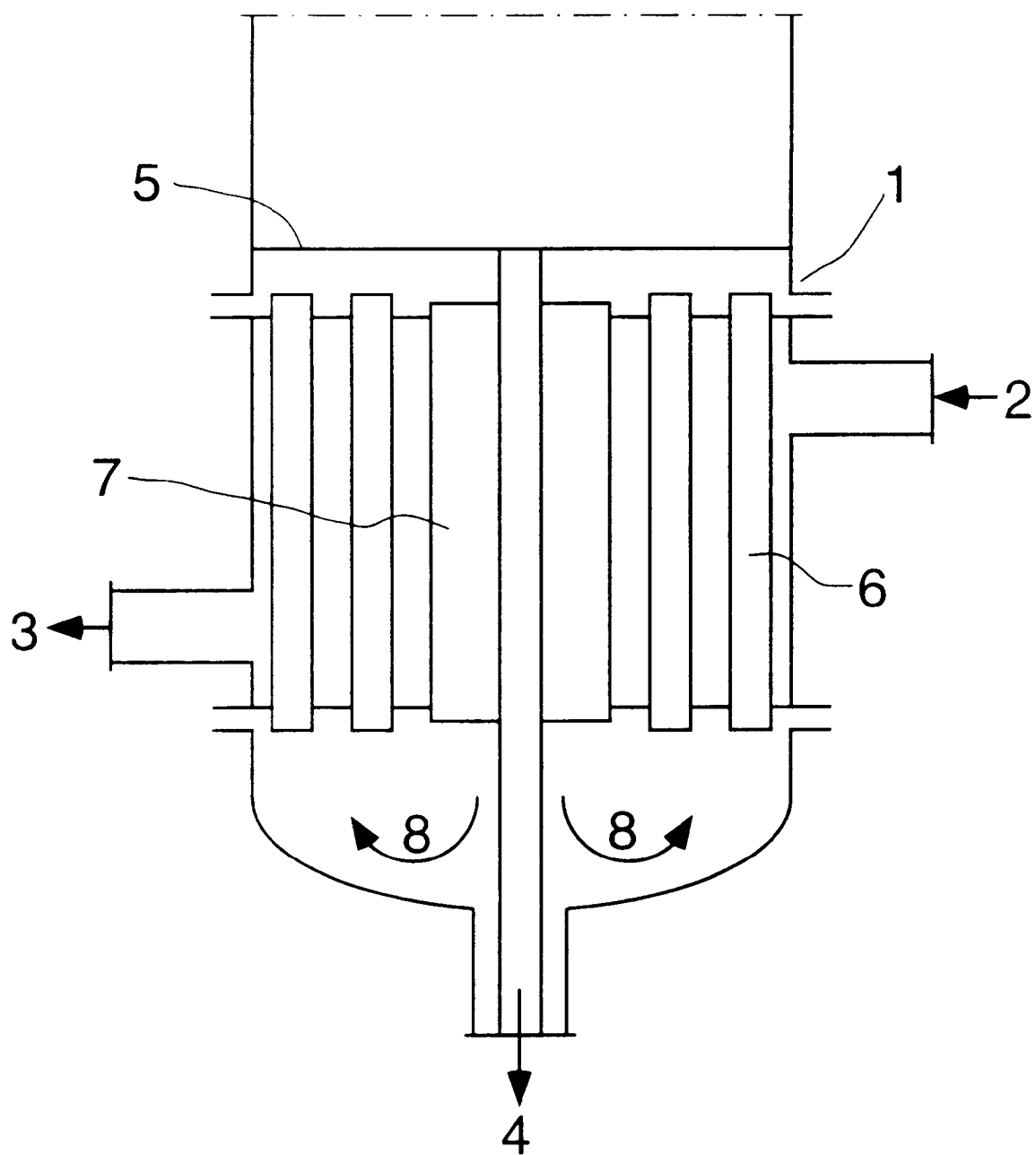
FIG. 2 shows a Roberts evaporator used in Example a).

EXAMPLE AND COMPARATIVE EXAMPLES a) Distillative single-phase flow separation of an acrylic acid which was obtained by gas-phase catalytic oxidation and was treated with aminoguanidine bicarbonate and to which phenothiazine and dodecylbenzenesulfonic acid had been added and which contained 99.25% by weight of acrylic acid, 0.2% by weight of dodecylbenzenesulfonic acid (for reducing the formation of coating), 500 ppm of acetic acid, 200 ppm of propionic acid, 10 ppm of low molecular weight aldehydes, 300 ppm of water, 200 ppm of phenothiazine (process polymerization inhibitor) and 2000 ppm of diacrylic acid, in a distillation apparatus consisting of a still, a condensation apparatus and a connection between still and condensation apparatus, a Robert evaporator as in FIG. 2 being integrated in the still (1=still, 2=heating steam, 3=heating steam condensate, 4=bottom product discharge, 5=liquid level, 6=evaporator pipe, 7=central fall pipe, 8=circulation direction).

The exact data of the distillation apparatus and of the mode of operation were as follows:

baffle-free stainless steel distillation column having only impact means and having an internal diameter of 1000 mm and a length of 4000 mm;

Robert evaporator having 351 stainless steel evaporator pipes (external diameter of the evaporator pipes=30 mm, wall thickness=2 mm, length=1200 mm);

feed of acrylic acid to be separated, directly into the still at a feed temperature of 25° C.: 3000 l/h;

pressure in the column: 70 mbar;

boiling point in the evaporator pipes: 75° C.;

4 bar heating steam at 151° C.;

steam consumption: about 800 kg/h;

removal of bottom product: 300 l/h.

About 2700 l/h of a condensate which contained 99.7% by weight of acrylic acid,

<1 ppm of phenothiazine,

<10 ppm of low molecular weight aldehydes and

<1000 ppm of diacrylic acid were obtained in the condenser, and hydroquinone monomethyl ether was added directly to said condensate as a storage stabilizer.

In the narrow evaporator pipes, the acrylic acid to be separated is transported upward by the resulting vapor bubbles and is conveyed down again in the central fall pipe (natural circulation).

Figure 3:
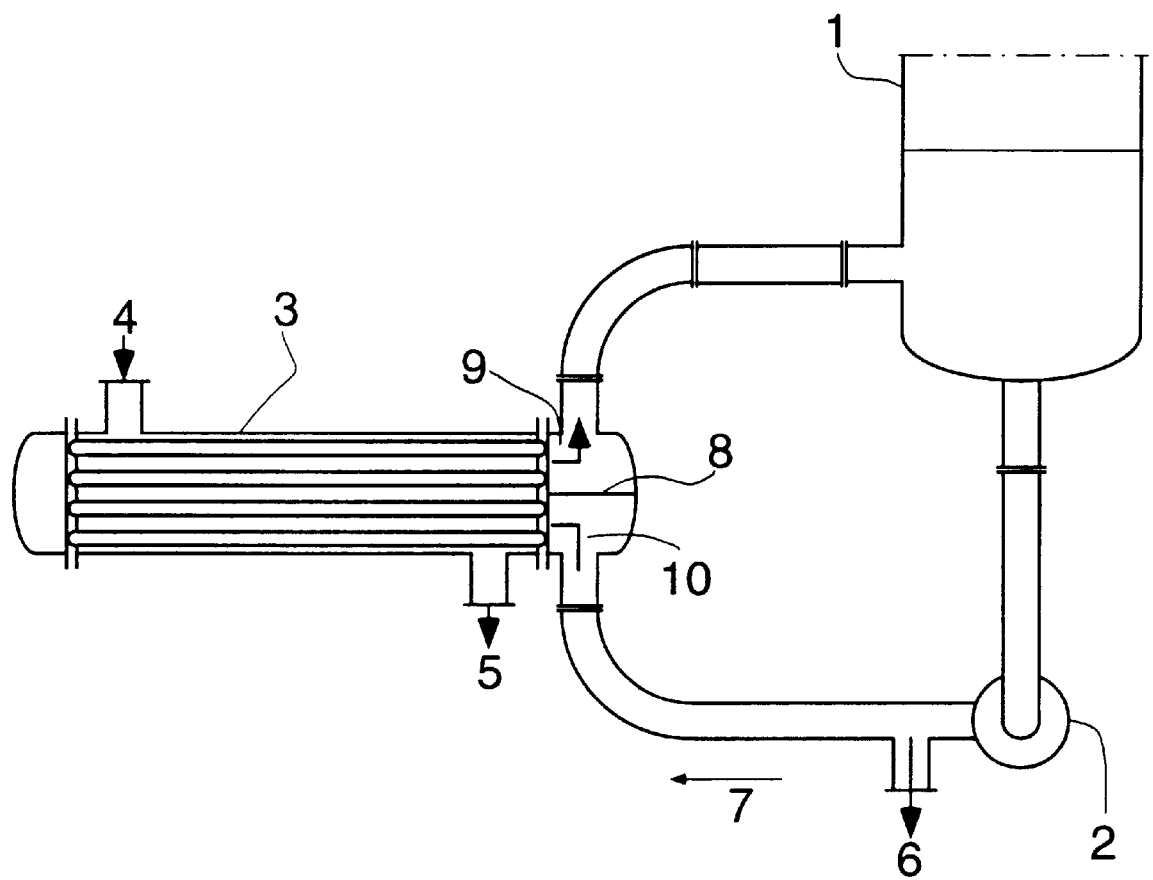
FIG. 3 shows a distillation apparatus used in Example b).

After continuous operation for 7 days, the distillation apparatus had to be shut down owing to blockage of the evaporator pipes.

b) Distillative single-phase flow separation of the same acrylic acid as in a) in a distillation apparatus consisting of a still, a condensation apparatus and a connection between still and condensation apparatus, the tube-bundle evaporator having been moved to a position outside the still, as in FIG. 3 (1=still, 2=circulation pump, 3=tubular evaporator, 4=heating steam, 5=heating steam condensate, 6=bottom product outlet, 7=circulation direction, 8=separation apparatus, 9=outflow, 10=inflow). The acrylic acid to be separated was transported by means of a circulation pump.

The exact data of the distillation apparatus and of the mode of operation were as follows:

baffle-free stainless steel distillation column having only impact means and having an internal diameter of 1000 mm and a length of 4000 mm;

tubular evaporator mounted outside and having 219 stainless steel evaporator pipes (external diameter of the evaporator pipes=30 mm, wall thickness=2 mm, length=3000 mm);

delivery of the circulation pump: 250 000 l/h;

flow velocity in the evaporator pipes: 1.4 m/sec;

feed of the acrylic acid to be separated, directly into the still at a feed temperature of 25° C.: 3000 l/h;

pressure in the column: 70 mbar;

boiling point in the evaporator pipes: 75.5° C. (owing to the additional hydrostatic pressure of the still liquid);

4 bar heating steam at 151° C.;

steam consumption: about 800 kg/h;

removal of bottom product: 300 l/h;

condensate obtained as in a).

The liquid boiling in the evaporator pipes was fed directly into the distilled liquid. After continuous operation for 20 days, the distillation apparatus had to be shut down owing to blockage of the evaporator pipes.

Distillative single-phase flow separation of the same acrylic acid as in a) in a distillation apparatus as in b), but which differed from b) in that the tubular evaporator was separated from the still on the pressure side by a throttle apparatus. The pressure thus built up in the tubular evaporator was 3 bar before the throttle (pump pressure) and prevented bubble formation therein as a result of boiling. The difference between the boiling point in the still (75° C.) and the temperature in the pipes of the tubular evaporator was 8K. The superheated liquid entered the still liquid directly.

After continuous operation for 4 months, the pipes of the tubular evaporator still had no coating.

We claim:

1. A process for the continuous distillative separation of liquid mixtures which contain (meth)acrylic acid as the main component, in a distillation apparatus which comprises a still, a condenser and a connection between still and condenser and to which the liquid mixture to be separated is continuously fed, wherein at least some of the energy required for evaporation of the liquid mixture is supplied to the distillation apparatus by a procedure in which a fraction of the liquid content present at a pressure $P_x$ in the still is continuously removed, said fraction is heated to a temperature to $T_y$ at a pressure $P_{y*}$ which is above $P_x$, with the proviso that $T_{y*}$ is above the boiling point $T_x$, associated with the pressure $P_x$, and below the boiling point $T_y$, associated with the pressure $P_y$, of the liquid content of the still, and that fraction of the still liquid which has been removed and superheated in this manner based on the pressure $P_x$ is then recycled to the distillation apparatus while letting down the pressure of said superheated liquid.

2. A process as claimed in claim 1, wherein the liquid mixture to be separated by distillation contains $\geq 95\%$ by weight of (meth)acrylic acid.

3. A process as claimed in claim 1, wherein the pressure in the still is from 10 to 150 mbar.

4. A process as claimed in claim 1, wherein the separation is carried out as a single-phase flow separation.

5. A process as claimed in claim 1, wherein the liquid mixture to be separated by distillation is continuously fed directly into the still.

6. A process as claimed in claim 1, wherein the superheated removed fraction of the still liquid is recycled directly to the still liquid.

7. A process as claimed in claim 1, wherein the difference between $P_y$ and $P_x$ is from 0.2 to 8 bar.

8. A process as claimed in claim 1, wherein $T_{y*}$ is from 3 to 12K above the temperature of the liquid content of the still.

9. A process as claimed in claim 1, wherein the superheating of the removed fraction of the still liquid is carried out in a tube-bundle heat exchanger.

10. A process as claimed in claim 1, wherein the liquid mixture to be separated by distillation contains phenothiazine and dodecylbenzenesulfonic acid in addition to (meth)acrylic acid.

\* \* \* \* \*